United States Patent [19]

Kolts et al.

[11] Patent Number: 4,775,654

[45] Date of Patent: Oct. 4, 1988

[54] COMPOSITION OF MATTER

[75] Inventors: John H. Kolts, Ochelata; James B. Kimble, both of Bartlesville, Okla.

[73] Assignee: Phillips Petroleum Company, Bartlesville, Okla.

[21] Appl. No.: 938,895

[22] Filed: Dec. 8, 1986

Related U.S. Application Data

[62] Division of Ser. No. 713,673, Mar. 19, 1985, Pat. No. 4,658,076.

[51] Int. Cl.$^4$ .................. B01J 23/04; B01J 23/06; B01J 23/14; B01J 27/135
[52] U.S. Cl. .................................. 502/226; 502/343; 502/352
[58] Field of Search .................. 502/226, 343, 352

[56]  References Cited

U.S. PATENT DOCUMENTS

| | | | |
|---|---|---|---|
| 3,419,633 | 12/1968 | Stapp | 502/226 X |
| 4,150,063 | 4/1979 | Besozzi et al. | 502/343 X |
| 4,368,346 | 1/1983 | Eastman | 585/658 |

*Primary Examiner*—W. J. Shine
*Attorney, Agent, or Firm*—Williams, Phillips & Umphlett

[57] ABSTRACT

A solid composition of matter selected from the group consisting of:

(a) a component comprising: (1) at least one material selected from the group consisting of Group IA metals and compounds containing said metals, a component comprising: (2) at least one material selected from the group consisting of zinc and compounds containing zinc, and a component comprising: (3) at least one material selected from the group consisting of chloride ions, compounds, containing chloride ions; tin and compounds containing tin; and (b) a component comprising: (1) at least one material selected from the group consisting of Group IA metals and compounds containing said metals, a component comprising: (2) zinc oxide, and, optionally, a component comprising: (3) at least one material selected from the group consisting of chloride ions, compounds containing chloride ions tin and compounds containing tin.

The above composition of matter is useful as a solid contact material adapted to convert feed organic compounds to product organic compounds, particularly, in the presence of a free oxygen containing gas.

A method for the conversion of feed organic materials to product organic materials, particularly methane to ethylene, in the presence of a free oxygen containing gas, utilizing combinations of Group IA metals, zinc and, optionally, chloride ions and/or tin, is also disclosed.

16 Claims, No Drawings

COMPOSITION OF MATTER

This application is a division of application Ser. No. 713,673, now U.S. Pat. No. 4,658,076.

The present invention relates to an improved composition of matter. In a more specific aspect, the present invention relates to a solid contact material for the oxidative conversion of feed organic compounds to product organic compounds, in the presence of a free oxygen containing gas, and a method for such conversion.

BACKGROUND OF THE INVENTION

Numerous processes are in use and have been proposed for the conversion of organic compounds and feedstocks to more valuable organic compounds and more valuable feedstocks for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectivity to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have at one time or another suggested that the function of the contact material involves a purely physical phenomenon, an adsorption-desorption process, either of atomic or molecular oxygen, either on the surface or occluded within the solid material, oxidation-reduction, utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen containing contact material, and, thereafter, reactivating or regenerating the contact material by again passing a free oxygen containing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that new and improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectivity to the desired products.

Of the various feedstocks for the organic chemical and petrochemical industries, olefins, such as ethylene and propylene are of particular interest and have become major feedstocks. Of these, ethylene is by far the more important chemical feedstock since the demand for ethylene feedstocks is about double that for propylene feedstocks. Consequently, there is a definite need for materials and processes for the conversion of relatively inexpensive feedstocks to ethylene. At the present time, ethylene is produced almost exclusively by the dehydrogenation or pyrolysis of ethane and propane, naptha and, in some instances, gas oils. About 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to catalyze pyrolytic reactions have been made. While some of these processes do, in fact, reduce the severity of the conditions, the conversion of the feedstock and the selectivity to ethylene are still quite low. Of particular interest in this phase of the art, is the oxidative conversion of methane to higher hydrocarbons, particularly ethylene and ethane and, more particularly, ethylene. However, these processes have, heretofore resulted in low conversions of methane and poor selectivity to ethylene and ethane.

SUMMARY OF THE INVENTION

It is therefore an object of the present invention to provide an improved composition of matter and method of utillizing the same which overcomes the above and other disadvantages of the prior art. Another object of the present is to provide an improved composition of matter. Still another object of the present invention is to provide an improved contact material for the oxidative conversion of organic compounds to other organic compounds, in the presence of a free oxygen containing gas. Another and further object of the present invention is to provide an improved method for the oxidative conversion of organic compounds to other organic compounds, in the presence of a free oxygen containing gas. Another and further object of the present invention is to provide an improved method for the oxidative conversion of alkane hydrocarbons to other hydrocarbons, in the presence of a free oxygen containing gas. A further object of the present invention is to provide a method for the oxidative conversion of organic compounds to other organic compounds which results in improved conversion of feedstock. Yet another object of the present invention is to provide a method for the oxidative conversion of organic compounds to other organic compounds which results in improved selectivity to desired products. A further object of the present invention is to provide a method for the oxidative conversion of organic compounds to other organic compounds which results in improved conversion of feedstock and an improved selectivity to desired products. Another and further object of the present invention is to provide a method for the oxidative conversion of organic compounds to other organic compounds which utilizes temperatures below those of known processes. A still further object of the present invention is to provide a method for the oxidative conversion of organic compounds to other organic compounds which reduces the energy requirements thereof. Another object of the present invention is to provide a method for the oxidative conversion of organic compounds to other organic compounds which can be carried out in a continuous manner. Yet another object of the present invention is to provide a method for the oxidative conversion of organic compounds to other organic compounds which extends the useful life of the contact material utilized. These and other objects of the present invention will be apparent from the following detailed description.

A solid composition of matter selected from the group consisting of:

(a) a component comprising: (1) at least one material selected from the group consisting of Group IA metals and compounds containing said metals, a component comprising: (2) at least one material selected from the group consisting of zinc and compounds containing zinc, and a component comprising: (3) at least one material selected from the group consisting of chloride ions, compounds containing chloride ions; tin and compounds containing tin; and (b) a component comprising: (1) at least one material selected from the group consisting of Group IA metals and compounds containing said metals, a component comprising: (2) zinc oxide, and, optionally, a component comprising: (3) at least one material selected from the group consisting of chloride ions, compounds containing chloride ions tin and compounds containing tin.

In still another aspect, the present invention relates to a solid contact material, of the above composition, adapted to convert feed organic compounds to product organic compounds, particularly in the presence of a free oxygen containing gas. The present invention further provides an improved method for the conversion of feed organic compounds to product organic compounds, comprising: contacting said feed organic compounds and a free oxygen containing gas with a solid contact material, comprising:

(a) a component comprising: at least one material selected from the group consisting of Group IA metals and compounds containing said metals;

(b) a component comprising: at least one material selected from the group consisting of zinc and compounds containing zinc; and, (c) optionally, a component comprising: at least one material selected from the group consisting of chloride ions, compounds containing chloride ions, tin and compounds containing tin, under oxidative conversion conditions sufficient to convert said feed organic compounds to said product organic compounds.

DESCRIPTION OF THE PREFERRED EMBODIMENTS

The improved composition of matter, of the present invention is a composition of matter selected from the group consisting of:

(a) a component comprising: (1) at least one material selected from the group consisting of Group IA metals and compounds containing said metals, a component comprising: (2) at least one material selected from the group consisting of zinc and compounds containing zinc, and a component comprising: (3) at least one material selected from the group consisting of chloride ions, compounds containing chloride ions; tin and compounds containing tin; and (b) a component comprising: (1) at least one material selected from the group consisting of Group IA metals and compounds containing said metals, a component comprising: (2) zinc oxide, and, optionally, a component comprising: (3) at least one material selected from the group consisting of chloride ions, compounds containing chloride ions tin and compounds containing tin.

Compositions, as set forth above, are useful as solid contact materials adapted to convert feed organic compounds to product organic compounds, particularly in the presence of a free oxygen containing gas.

The present invention further provides an improved method for the conversion of feed organic compounds to product organic compounds, comprising: contacting said feed organic compounds and a free oxygen containing gas with a solid contact material, comprising:

(a) a component comprising: at least one material selected from the group consisting of Group IA metals and compounds containing said metals;

(b) a component comprising: at least one material selected from the group consisting of zinc and compounds containing zinc; and (c), optionally, a component comprising: at least one material selected from the group consisting of chloride ions, compounds containing chloride ions, tin and compounds containing tin, under oxidative conversion conditions sufficient to convert said feed organic compounds to said product organic compounds.

The Group IA metals are preferably selected from the group consisting of lithium, sodium and potassium.

When the term "effective amount" is utilized with reference to the composition of matter or contact materials herein, this term is meant to include more than an insignificant amount and, thus, a small amount sufficient to affect the function of the composition of matter for the purpose for which it is to be utilized.

Thus, the above compositions of matter or contact materials contain from an effective amount of the Group IA metal to near 100 wt. %, so long as an effective amount of zinc is present, usually from about 0.1 wt. % to about 50wt. % of the Group IA metal (expressed as elemental metal) and, preferably, between about 0.5 wt. % and about 15 wt. % and still more preferably, between about 1 wt. % and about 5 wt. %. Where tin is utilized, it is present in an effective amount to near 100 wt. %, usually in amounts between about 0.5 wt. % and 20 wt. %, preferably between about 1 wt. % and about 7 wt. %, expressed as elemental tin. Chloride, when present, is utilized in amounts from an effective amount to near 100 wt. %, usually between about 0.1 wt. % and about 5 wt. %, expressed as elemental chlorine. The weight percent designations given are the weight percent of the indicated element based on the total weight of the active components of the composition of matter or contact materials, including the zinc compound and the compound or compounds in which the element or elements are present.

The above-mentioned components can be mixed with or deposited on an "inert support material" adapted to harden or support the active materials. The term "inert support material" when utilized in this context is meant to include any material which does not react with or exchange ions with the active components, has no significant functional effect on the production of desired or undesired products in the process for which the solid contact material is utilized and functions only as a hardening agent or support for the active components. Where such solid support material is utilized, the weight of such solid support material is not included in determining the relative weights of the active components.

The Group IA metal, tin, chloride and zinc can be derived from any suitable source of such materials, such as compounds of the Group IA metal, tin, chloride and zinc which are in the form of carbonates, hydroxides, oxides, nitrates, octoates, chlorides, etc. The compositions of matter and contact materials can be prepared by any suitable method known in the art for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. For example, a lithium/zinc material may be produced by mixing lithium carbonate and zinc oxide in a blender with enough water to form a thick slurry. The slurry can then be dried, usually at a temperature sufficient to volatilize the water or other carrier, such as about 220° F. to about 450° F. Alternatively, zinc oxide pellets can be impregnated with an aqueous solution of lithium nitrate and dried. Where tin is present, the composition can be produced by impregnating zinc oxide pellets with a hexane solution of tin octoate and drying. Lithium/tin/zinc compositions can be produced by impregnating zinc oxide pellets with a hexane solution of tin octoate and an aqueous solution of lithium nitrate and drying. In all cases, irrespective of how the components are combined, and irrespective of the source of the metal or chloride, the dried composition is calcined in the presence of a free oxygen containing gas, usually at temperatures between about 700° F. and about 1200° F. for from 1 to about 24 hours. While the exact form of the metals in the resultant composition and contact materials is not known, it is believed that the Group IA and zinc are predominantly in their oxide form and, where chlorine is present, it is in the form of a chloride. When both tin and chloride ions are added a convenient component is tin chloride.

These compositions of matter and contact materials are particularly useful for the oxidative conversion of feed organic compounds to product organic compounds, in the presence of a free oxygen containing gas. Processes of this character include the oxidative dehydrogenation of hydrocarbons, particularly alkanes having 2 to 7 carbon atoms, to other hydrocarbons, particularly ethylene, the oxidative methylation of toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The compositions of matter and contact materials of the present invention are particularly useful for the oxidative conversion of methane to higher hydrocarbons, particularly the oxidative conversion of methane to ethylene, in the presence of a free oxygen containing gas.

The conditions of operation of such processes for the oxidative conversion of feed organic compounds to product organic compounds can vary over a wide range. Such conditions are either known to those skilled in the art or can be readily optimized by one skilled in the art by simple, conventional experiments.

Since the composition of matter and contact materials of the present invention are highly effective for the oxidative conversion of methane to higher hydrocarbons, particularly ethylene and ethane, and this process is of great value, the conversion of feed organic materials to product organic materials will be illustrated and exemplified by such methane conversion.

In accordance with most previous theories of the function and operation of contact materials for the oxidative conversion of methane to higher hydrocarbons, and particularly ethylene and ethane, the reaction has been carried out in the absence of a free oxygen containing gas, with the oxygen theoretically being supplied by the contact material. As a result, the most utilized modes of operation have included treating the contact material with a free oxygen containing gas, such as oxygen or air, for a period of time sufficient to produce a reducible oxide of a multivalent metal, thereafter, contacting methane with the reducible metal oxide and, thereafter, treating the metal oxide with a free oxygen containing gas to "regenerate" the same. Similarly, certain contact materials are contacted with a free oxygen containing gas to cause adsorption of oxygen on the contact material, methane is, thereafter, contacted with the contact material containing adsorbed oxygen and, thereafter, the contact material is again treated with a free oxygen containing gas. In both instances, the contact material, after treatment with a free oxygen containing gas, is usually purged with an inert gas, such as nitrogen, to remove excess oxygen which has not reacted with or been adsorbed on the contact material. Consequently, several techniques have been followed, including, carrying out the contact with methane and the contact with a free oxygen containing gas in separate reaction chambers or sequentially passing a free oxygen containing gas, a purge gas and methane through the contact material in a single reaction vessel. The disadvantages of either of these procedures will be evident to one skilled in the art.

In contrast to these prior art techniques, the method of the present invention is carried out by contacting methane with a contact material, in the presence of a free oxygen containing gas.

In addition to methane, the hydrocarbon feedstock, employed in the method of the present invention, may contain other hydrocarbon or non-hydrocarbon components. The presence of ethane, propane and the like is not detrimental. It has been found that carbon dioxide and water are not detrimental, since they are most often products of the process. It has also been found that inert gases, such as nitrogen, helium and the like are not detrimental. Consequently, the method of the present invention can effectively utilize any conventional natural gas. To the extent that significant amounts of hydrogen sulfide are present in the natural gas, it is desirable to first remove the hydrogen sulfide, since it is believed that excessive amounts of this material can be detrimental to the method. Accordingly, a relatively inexpensive source of methane, namely natural gas, can be employed without expensive separation or processing of the components thereof, with the exception of the relatively inexpensive removal of excess amounts of hydrogen sulfide. Other sources of methane or methane-containing gases can also be utilized.

The free oxygen containing gas may be any suitable oxygen containing gas, such as oxygen, oxygen-enriched air or air. The method of the present application has been effectively carried out utilizing air as a source of oxygen.

When utilized in the present invention, the term "diluent gas" is meant to include any gaseous material present in the methane-containing gas, the free oxygen containing gas or in the form of an added gas which is essentially inert with respect to the oxidative conversion of methane and, thus, does not significantly decrease the conversion of methane and/or the selectivity to the production of higher hydrocarbons.

The volumetric ratio of methane to free oxygen should be in excess of about 1/1, preferably it is between about 1/1 and about 30/1 and still more preferably between about 4/1 and about 15/1. It has been found that a ratio of methane to free oxygen of at least about 1/1 is necessary, in accordance with the present invention, in order to obtain maximum conversion of methane and high selectivity to higher hydrocarbons, particularly ethylene.

Where combinations of lithium, sodium, potassium or mixtures thereof and zinc and optional tin and chloride are referred to herein, the zinc will be referred to as the "base metal", whereas the lithium, sodium, potassium, Group IA metal, tin or chloride will be referred to as the "promoter", strictly as a matter of convenience, based on the fact that the "promoter" is generally the minor component of the contact material. It is to be clearly understood that such designations are not utilized to define the function or operation of the material, since the junctions of the contact materials are not fully understood. In most instances, both metal components are necessary and appear to be active components in the conversion of methane to higher hydrocarbons. It has also been found that the presence of chloride ions in the contact material has a beneficial effect in the oxidative conversion of methane to higher hydrocarbons. The chloride ion may be present as a part of a compound of either the promoter metal or the base metal or as part of a separate compound. It has further been found that the presence of tin or a tin compound in the contact material also has a beneficial effect in the oxidative conversion of methane to higher hydrocarbons. Both chloride ions and tin are still more beneficial. Accordingly, a convenient form of these ingredients is in the form of tin chloride deposited on the base metal or mixed therein.

In the present invention, it has been found that the method can be carried out between two extremes, namely, low conversion of methane/high selectivity to higher hydrocarbons, particularly ethylene, and high conversion of methane/low selectivity to the higher carbons, particularly ethylene. The process parameters (space velocity, temperature, and reactant partial pressure) can, to some extent, be used to control the reaction at the desired point between these two limits. Consequently, the reaction conditions may vary between broad limits.

The temperature is preferably at least about 500° C. and will generally vary between about 500° C. and about 1500° C. However, in order to obtain high conversions of methane and high selectivities to ethylene and ethane, the temperature is preferably between about 500° C. and about 900° C. and most desirably between about 600° C. and about 800° C.

It has also been found that, as the partial pressure of oxygen is increased, the selectivity to higher hydrocarbons decreases and the selectivity to carbon dioxide increases and vice versa. Total pressures may vary anywhere from around 1 atmosphere to about 1500 psi but are preferably below about 300 psi and ideally below about 100 psi.

Methane flow rates can also vary over a wide range, for example, from 0.5 to 100 cubic centimeters per minute per cubic centimeter of contact material. Preferably, however, the rate is between about 1.0 and about 75 cubic centimeters per minute per cubic centimeter of contact material.

The total flow velocities of all gaseous materials, including diluents, through a fixed bed reactor, may be at any rate effective for the oxidative conversion reaction. For example from 50 to 10,000 GHSV and preferably from 500 to 5000 GHSV.

In addition to the high conversion of methane and high selectivity to ethylene and ethane, attainable in accordance with the present invention, the contact materials are not readily poisoned and will tolerate the presence of water, carbon dioxide, carbon monoxide and the like. In addition, the contact materials appear to be long lived, with no noticeable deactivation problems. Concomitantly, the process can be carried out continuously in fixed, moving, fluidized, ebullating or entrained bed reactors.

The following examples illustrate the nature and advantages of the present invention.

The contact materials of the examples were prepared by aqueous slurrying, drying and calcination.

In the runs of the examples, the contact material was loaded in a quartz reactor having a thermocouple well centered in the contact material bed. The reactor was brought up to temperature under nitrogen or air and thereafter methane and air (or oxygen) flow was begun. The gas inlet system included electronic flow measurement, a three-zone furnace for heating reactant gases and the contact material and a downstream analysis system. The reactor effluent was snap sampled, at any desired time, and analyzed for all paraffins and olefins between $C_1$ and $C_4$ and $N_2$, $O_2$, CO and $CO_2$, by gas chromatography. All contact materials are referred to in terms of weight percent of the designated element, based on the total weight of contact material.

The variables and results of this series of tests are set forth in the Table below. Conversion is mole percent of methane converted. Selectivity and yields are based on mole percent of methane feed converted to a particular product. The $CH_4$ rate can be expressed as cc/min/cc of contact material. For example, when 70 cc/min of $CH_4$ was fed to a reactor containing 20 cc of catalyst the flow rate would be 3.5 cc/min of $CH_4$/cc of contact material. The volumetric ratio of $CH_4$ to oxygen or other gas is also given in terms of cc/min of $CH_4$ per cc/min of other gases (air or $N_2$ etc.) present. The promoter metals of the contact materials were in their oxide form and, as previously indicated, the percent of promoter metal is the weight percent of elemental promoter metal or metals based on the total weight of the promoter metal compound or compounds and the base metal compound.

TABLE

| Run No. | Contact Material | Volume | Volume of Con. Mat. | Sample Time (min) | Temp (°C.) | Conversion | Selectivity % | | | | | | |
|---|---|---|---|---|---|---|---|---|---|---|---|---|---|
| | | | | | | | $C_2=$ | $C_2$ | $C_2$'s | $C_3=$ | $C_3$ | $CO_2$ | CO |
| | | $CH_4$/Air | | | | | | | | | | | |
| 1 | Li(3%)/ZnO | 70/80 | 20 cc | 5 | 711 | 11.4 | 41.3 | 46.3 | 87.6 | 3.5 | 1.5 | 7.5 | — |
| | | | | 40 | 716 | 11.3 | 38.9 | 45.4 | 84.3 | 3.3 | 1.3 | 8.8 | 2.3 |
| | | | | 80 | 717 | 10.1 | 34.4 | 46.6 | 81 | 2.7 | 1.4 | 12 | 2.8 |
| | | | | 114 | 744 | 16.2 | 37 | 29.1 | 66.1 | 3.6 | — | 27.4 | 2.9 |
| | | | | 165 | 745 | 17.4 | 37.5 | 29.3 | 66.8 | 3.6 | 0.9 | 25.5 | 3.1 |
| 2 | | 80/80 | | 15 | 715 | 18.5 | 39.5 | 34 | 73.5 | 2.7 | 1 | 20.5 | 2.3 |
| | | 150/150 | | 15 | 714 | 12.6 | 32.4 | 41.9 | 74.3 | 2.3 | — | 23.4 | — |
| | | 150/150 | | 105 | 717 | 12.6 | 31.5 | 41.5 | 73 | 1.9 | — | 25 | — |
| | | 225/225 | | 15 | 720 | 9.4 | 27.7 | 50.5 | 78.2 | — | — | 21.8 | — |
| | | 300/300 | | 15 | 714 | 8 | 23.3 | 53.5 | 76.8 | — | — | 23.2 | — |
| Constant flow of 300 cc/min but different ratios of $CH_4/O_2$ with make-up $N_2$ | | | | | | | | | | | | | |
| | | $CH_4/O_2/N_2$ | | | | | | | | | | | |
| 3 | Li(3%)/ZnO | 150/30/120 | 20 cc | 30 | 719 | 12.5 | 31.6 | 41.7 | 73.3 | 2.4 | 1.2 | 23 | — |
| | | 150/24/126 | | 30 | 714 | 11.5 | 32.4 | 45.4 | 77.8 | 2.4 | — | 19.8 | — |
| | | 150/18/132 | | 30 | 707 | 11.3 | 30.7 | 46 | 76.7 | 2.3 | 1.9 | 19 | — |
| | | 150/12/138 | | 30 | 714 | 8.8 | 30.2 | 53.2 | 83.3 | — | — | 16.6 | — |
| | | 150/8/142 | | 60 | 711 | 7.6 | 27.7 | 55.4 | 83.1 | 1.9 | 2.2 | 12.8 | — |
| | | 150/8/142 | | 160 | 756 | 8.9 | 33.7 | 48.3 | 82 | — | — | 18 | — |
| | | 150/8/142 | | 220 | 758 | 9.1 | 34.9 | 47.3 | 82.2 | 2.9 | 1.7 | 13.2 | — |
| | | 150/8/142 | | 260 | 758 | 8.4 | 37.8 | 51.9 | 89.7 | — | — | 10.3 | — |
| With steam as diluent instead of $N_2$. Steam to hydrocarbon ratio is 1/1. | | | | | | | | | | | | | |
| | | $CH_4/O_2$ | | | | | | | | | | | |
| 4 | Li(3%)/ZnO | 150/15 | 20 cc | 5 | 721 | 12 | 38.5 | 39.3 | 77.8 | 3.6 | 1.9 | 16.7 | — |
| | | | | 45 | 728 | 11.4 | 42.1 | 41.1 | 83.2 | 4.2 | 1.8 | 10.8 | — |
| | | | | 80 | 728 | 11.6 | 39.3 | 39.4 | 78.7 | 3.7 | 1.8 | 15.7 | — |
| | | | | 115 | 729 | 11.4 | 42.1 | 40.6 | 82.7 | 4.2 | — | 13.1 | — |
| | | | | 220 | 728 | 11.6 | 40.4 | 41.3 | 81.7 | 3.5 | — | 14.5 | 0.4 |
| | | *150/0 | | 8 | 717 | 1.4 | — | — | — | — | — | 100 | — |
| | | *150/0 | | 50 | 721 | 0.7 | — | — | — | — | — | 100 | — |
| $CH_4$ and $O_2$ no other diluent present | | | | | | | | | | | | | |
| 5 | Li(3%)/ZnO | 150/10 | 20 cc | 15 | 716 | 9.1 | 42.4 | 46.7 | 89.1 | 4.4 | 4.3 | 2.2 | — |
| | | | | 50 | 713 | 8.3 | 44.9 | 44.6 | 89.5 | 5.1 | 2.1 | 3.3 | — |
| | | 150/15 | | 8 | 715 | 9.4 | 43.9 | 42.2 | 86.1 | 4.7 | 1.8 | 7.3 | — |
| | | | | 50 | 713 | 11.2 | 39.9 | 35.6 | 75.5 | 4 | — | 18.3 | 2.1 |
| | | | | 85 | 713 | 10.5 | 40.5 | 37.1 | 77.6 | 4.3 | — | 18 | — |
| 6 | Na(3%)/ZnO | 96/96 | 23 | 18 | 704.0 | 11.6 | 18.1 | 36.7 | 54.8 | — | — | 45.2 | — |
| | | | | 60 | 700.0 | 10.5 | 16.6 | 37.3 | 53.9 | — | — | 46.1 | — |
| | | | | 120 | 701.0 | 10.6 | 16.0 | 37.0 | 53.0 | 1.0 | 0.9 | 45.2 | — |
| 7 | (K(3%)/ZnO | 104/104 | 25 | 7 | 701.0 | 12.3 | 5.0 | 17.8 | 22.8 | — | — | 77.3 | — |
| | | | | 43 | 702.0 | 12.6 | 6.3 | 19.6 | 25.9 | — | — | 74.1 | — |
| | | | | 90 | 702.0 | 12.8 | 6.4 | 19.7 | 26.1 | — | — | 73.8 | — |
| | | | | 126 | 701.0 | 13.1 | 6.2 | 19.4 | 25.6 | — | 2.8 | 71.7 | — |
| 8 | Quartz | 70/80 | 20 | 40 | 740.0 | — | — | — | — | — | — | — | — |
| 9 | $Zn_2TiO_4$ | 70/80 | 20 | 40 | 717.0 | 11.0 | 2.0 | — | — | — | — | 91.0 | 7.0 |

*Steam was utilized but no oxygen.

It has also been found that the production of $CO_2$ was high and, hence, the HC selectivity was low, if the concentration of $O_2$ in the initial feed stream is high. Accordingly, the HC selectivity can be increased and the $CO_2$ production concomittantly decreased by staged addition of the free oxygen containing gas to provide an effective portion of the total $O_2$ at a plurality of spaced points along a continuous contact material bed or between separate contact material beds.

While specific materials, conditions of operation, modes of operation and equipment have been referred to herein, it is to be recognized that these and other specific recitals are for illustrative purposes and to set forth the best mode only and are not to be considered limiting.

That which is claimed:

1. A solid composition of matter consisting essentially of: (1) at least one material selected from the group consisting of Group IA metals and compounds containing said metals, (2) at least one material selected from the group consisting of zinc and compounds containing zinc, and (3) at least one material selected from the group consisting of chloride compounds, tin and compounds containing tin.

2. A composition in accordance with claim 1 wherein the Group IA metal is selected from the group consisting of lithium, sodium and potassium.

3. A composition in accordance with claim 1 wherein the Group IA metal is predominately in the oxide form.

4. A composition in accordance with claim 1 wherein the zinc is predominantly in the oxide form.

5. The composition in accordance with claim 1 wherein the Group IA metal is present in an amount between about 0.1 weight percent and about 50 weight percent, expressed in terms of the element based on the total weight of said composition.

6. A composition in accordance with claim 1 wherein said at least one material selected from the group consisting of chloride compounds, tin and compounds containing tin is tin chloride.

7. A composition in accordance with claim 1 wherein said composition is formed by:
    (a) combining at least one compound of the Group IA metal, at least one compound of zinc, and at least one material selected from the group consisting of at least one compound of tin and at least one chloride compound; and
    (b) calcining the thus combined compounds in the presence of a free oxygen containing gas.

8. A composition in accordance with claim 7 wherein said combined compounds are combined as an aqueous slurry.

9. A composition in accordance with claim 7 wherein said combined compounds are selected from the group consisting of carbonates, hydroxides, oxides, nitrates, octoates and chlorides.

10. A composition in accordance with claim 1 wherein the Group IA metal is predominately in the form of a compound selected from the group consisting of carbonates, hydroxides, oxides, nitrates, octoates and chlorides.

11. A composition in accordance with claim 1 wherein said at least one material selected from the group consisting of chloride compounds, tin and compounds containing tin is at least one chloride compound.

12. A composition in accordance with claim 1 wherein said at least one material selected from the group consisting of chloride compounds, tin and compounds containing tin is a compound containing tin.

13. A composition in accordance with claim 11 wherein said at least one chloride compound is present in an amount between about 0.1 weight percent and about 5 weight percent, expressed in terms of elemental chlorine based on the total weight of said composition.

14. A composition in accordance with claim 12 wherein tin is present in an amount between about 0.5 weight percent and about 20 weight percent, expressed in terms of the element based on the total weight of said composition.

15. A solid contact material, adapted to convert feed organic compounds to product organic compounds, consisting essentially of: (1) at least one material selected from the group consisting of Group IA metals and compounds containing said metals, (2) at least one material selected from the group consisting of zinc and compounds containing zinc, and (3) at least one material selected from the group consisting of chloride compounds, tin and compounds containing tin.

16. A contact material in accordance with claim 15 wherein said contact material is adapted to convert feed organic compounds to product organic compounds in the presence of a free oxygen containing gas.

* * * * *